(12) United States Patent
Shirasu et al.

(10) Patent No.: US 6,919,082 B2
(45) Date of Patent: Jul. 19, 2005

(54) PHARMACOLOGICAL COMPOSITION CONTAINING YEAST CELL WALL FRACTION

(75) Inventors: Yoshiharu Shirasu, Takasaki (JP); Tomohiko Nakamura, Takasaki (JP); Hideyuki Wakabayashi, Takasaki (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 282 days.

(21) Appl. No.: 10/267,663

(22) Filed: Oct. 10, 2002

(65) Prior Publication Data

US 2003/0118607 A1 Jun. 26, 2003

Related U.S. Application Data

(63) Continuation of application No. 09/781,444, filed on Feb. 13, 2001, now abandoned.

(51) Int. Cl.$^7$ .............................................. A61K 35/72
(52) U.S. Cl. ................................................. 424/195.16
(58) Field of Search ...................................... 424/195.16

*Primary Examiner*—Jean C. Witz
(74) *Attorney, Agent, or Firm*—Venable LLP; Ann S. Hobbs; Robert Kinberg (57) ABSTRACT

The present invention provides a pharmacological composition as a composition as a raw material capable of preventing or treating the symptoms of inflammatory bowel diseases such as ulcerative colitis, constipation, allergic diseases such as atopic dermatitis, and so on, and which has little side effect and thereby safe, high water dispersibility, and can be ingested easily.

A yeast cell wall fraction, which comprises yeast extracts residue and being superior in water dispersibility and swelling properties, is used as an active constituent. As a yeast cell wall fraction, a yeast cell wall fraction obtained with a simple operation of water cleansing of yeast cell after alkali processing yields superior effects for preventing or treating the symptoms of inflammatory bowel diseases such as ulcerative colitis, constipation, allergic diseases such as atopic dermatitis, and so on, as well as such yeast cell wall fraction without foreign taste and odor characteristic to autolysis and suitable for ingestion.

8 Claims, 6 Drawing Sheets

1. Cellulose
2. Yeast Cell Wall Fraction
3. Glucomannan
4. Galactomannan
5. β-1,3-glucan
6. Dried Yeast

Edema Ratio (%)

FIG. 7

Tumidity (mm)

PHARMACOLOGICAL COMPOSITION CONTAINING YEAST CELL WALL FRACTION

This Appl. is a CON of Ser. No. 09/781,444 Feb. 13, 2001, now abandoned.

BACKGROUND OF THE INVENTION

1. Field of the Invention

The present invention generally relates to a pharmacological composition containing cell residue obtained by removing soluble cell substance from enzymegenated yeast, preferably cell residue obtained by conducting water cleansing after alkali treatment, and having as its active constituent a yeast cell wall fraction containing abundant protein and dietary fiber. Particularly, the present invention relates to an agent and/or a food product having as its active constituent the aforementioned yeast cell wall fraction and capable of preventing and/or treating the symptoms of inflammatory bowel diseases such as ulcerative colitis, constipation, allergic diseases such as atopic dermatitis, and so on.

2. Description of the Related Art

Conventionally, as technology directed to a pharmacological composition having as its active constituent yeast or a yeast cell component substance, known are a manufacturing method of a polysaccharide ester sulfate compound and the alkali metal saline thereof having a anti-digestive ulcer agent effect and an anti-arterial sclerosis effect, obtained by sulfating a yeast cell wall in a basic organic solution with chlorosulphonic acid or sulfur trioxide, or sulfating a yeast cell wall by blending it with cooled and levigated strong sulfuric acid and thereafter making it an alkali salt (Japanese Patent Application Laid-Open No. 49-48894); a manufacturing method of a polysaccharide ester sulfate compound and the alkali metal saline thereof obtained by sulfating a yeast cell wall in a basic organic solution with chlorosulphonic acid or sulfur trioxide, or sulfating a yeast cell wall by blending it with cooled and levigated strong sulfuric acid and thereafter making it an alkali salt (Japanese Patent Application Laid-Open No. 56-31955); a manufacturing method of a new physiologically active substance peptide mannan A which extracts peptide mannan A from a yeast cell belonging to Saccharomyces and ingests peptide mannan A from such extract (Japanese Patent Laid-Open Publication No. 49-69808); a manufacturing method of a compound protein SP-1 having an anti-ulcer effect and containing amino acids and mannose by making the pepsin act upon the yeast cell wall (Japanese Patent Application Laid-Open No. 62-39527); an anti-allergic agent having as its active constituent mannan deriving from yeast and the like (Japanese Patent Application Laid-Open No.63-119427); an anti-ulcer agent having as its active constituent dried brewer's yeast with no concern of side effects as it is a natural product (Japanese Patent Application Laid-Open No. 1-313434); a nutrition supplement composition to be administered to mammals and containing a sufficient amount of β-glucan deriving from yeast for supplying a fiber source in foods, fecal-increasing agent, and short-chain fatty acid, and which improves the digestion in mammals, decreases the serum cholesterol level, and fortifies the decrease in weight (Japanese Patent Application Laid-Open No. 4-505997); food, beverage and medical product containing magnesium supplement material which connotes magnesium salt within a yeast cell wall prepared by eluting and separating intercellular cell constituents (Japanese Patent Application Laid-Open No. 9-107919); an inhibitor of antibody-producing cell containing yeast-related polymer, and a composition such as food or medical product for autoimmune disease containing this inhibitor of antibody-producing cell (Japanese Patent Laid-Open Publication No. 9-188626); and a skin condition improving composition suitable for preventing and treating the likes of atopic dermatitis and containing protease hydrolysate of brewer's yeast and diuretic (Japanese Patent Laid-Open Publication No. 9-227390).

Further, conventionally, as technology directed to making the autolytic residue of yeast tasteless and odorless, known are a method of improving the flavor of brewer's yeast by moisture distillation and organic solvation of brewer's yeast (Japanese Patent Application Laid-Open No. 63-22177), a method of decolorizing and deodorizing yeast extract residue, or yeast autolytic residue, wherein yeast extract residue is processed with alkali and acid, high concentration ozone treatment is conducted thereafter, and ethanol treatment is further implemented (Japanese Patent Application Laid-Open No. 4-248968); a method of reducing the foreign taste and odor characteristic to yeast by conducting acid treatment and heat treatment to yeast or a yeast-processed product (Japanese Patent Application Laid-Open No. 6-70751); and a method of making a yeast autolytic insoluble substance tasteless and odorless by suspending a yeast autolytic insoluble substance in ethanol, carrying the stirring treatment under alkaline conditions and eluting the causative agent of foreign taste and odor thereby, and eliminating the eluted material pursuant to centrifugation and eliminating the foreign taste and odor characteristic to a yeast autolytic insoluble substance thereby (Japanese Patent Application Laid-Open No. 9-103266). In addition, as technology directed to the treatment method of yeast cells and yeast cell walls, known is a manufacturing method of a seasoning wherein yeast cells are crushed with a high-pressure spray-impact homogenizer, hot water extraction is conducted thereto, and centrifugation is performed to the yeast cell walls which could not be made into particulates (Japanese Patent Application Laid-Open No. 9-117263).

Meanwhile, as technology directed to a preventive or treating agent for ulcerative colitis, which is a representative example of sudden inflammatory bowel disease, with its predominant symptoms being severe diarrhea, severe mucous and bloody diarrhea, and abdominal pain, and which causes erosion to the entire large intestine and damage to the mucous membrane such as ulcer, known are a composition containing a substance, separated from barley malts or rice germinated seeds and containing protein and insoluble dietary fibers and soluble dietary fibers, and which comprises the functions of an intestinal mucous membrane enhancer, defecation promoter and an agent for controlling the intestinal functions (Japanese Patent Application Laid-Open No. 9-278664); a preventive or treating agent having as its active constituent trehalose for symptoms of ulcerative colitis (Japanese Patent Application Laid-Open No. 10-17478); and a preventive and/or treating agent for inflammatory bowel diseases having as its active constituent catechin and nutrition composition containing the above (Japanese Patent Application Laid-Open No. 11-116475).

In recent years, short-chain fatty acids produced by the fermentation of intestinal bacteria in the digestive organs are attracting attention. When dietary fibers are ingested, they are assimilated at the large intestine by intestinal bacteria, and transformed to short-chain fatty acids, which are fermentation products. The generated short-chain fatty acids are promptly absorbed by the intestinal tract, and is said to act as the energy source of the large intestine and contribute to the normalization and activation of the large intestinal function. Among the short-chain fatty acids, butyric acid is particularly an important substance for the epithelial cells of the large intestine, and plays an important role in the maintenance and fortification of the structure and function of large intestine epithelial cells. It is therefore considered that butyric acid is important for preventing or treating the symptoms of inflammatory bowel diseases such as carcinoma of the colon and rectum, ulcerative colitis, and Crohn's disease.

As the raw material for promoting the production of such short-chain fatty acids, known are intestinal bacteria such as bifidobacteria and acidophilus which is said to improve the intestinal environment, and oligosaccharide which is the growth promotion factor thereof, and these have been conventionally used as the raw material for contributing to the regulation of the intestinal function. Nevertheless, even if intestinal bacteria such as bifidobacteria or acidophilus is ingested, there is a problem in that most of such bacteria dies before reaching the large intestine as a result of the effect of gastric acid, and would not contribute to the high production of short-chain fatty acids. Moreover, upon ingesting oligosaccharide, although it would produce short-chain fatty acids by being assimilated with intestinal permanent bacteria, there is a problem in that large volumes of expensive oligosaccharide must be ingested for high product of short-chain fatty acids. In addition, it has been indicated that another element for the high production of short-chain fatty acids is the swelling of assimilated substances in the intestine such that the intestinal bacteria can operate more easily.

Today, in addition to the prevention and cure of the aforementioned inflammatory bowel diseases such as ulcerative colitis, attracting attention is the prevention and cure of diseases characteristic to contemporary people; for example, allergic diseases such as atopic dermatitis, constipation, and so on. Particularly, the prevention and cure with ingestion of simple health foods with little side effects is attracting attention. Meanwhile, the autolytic residue obtained from the autolysis of yeast cells has a foreign taste and odor characteristic to autolytic residue, and although this has been used as foodstuff for fish farming and the like, it is necessary to eliminate such characteristic taste and odor for easier indigestion upon using the same as raw material for food products. Thus, an object of the present invention is to satisfy these needs, and to provide is a pharmacological composition as a raw material capable of preventing or treating the symptoms of inflammatory bowel diseases such as ulcerative colitis, constipation, allergic diseases such as atopic dermatitis, and so on, and which has little side effect and thereby being safe, high water dispersibility, and can be ingested easily.

During the research process on a yeast cell wall fraction which is the extract residue of yeast extracts, the present inventors have coincidentally discovered that a yeast cell wall fraction, regardless of it containing insoluble dietary fibers, is superior in water dispersibility and swelling properties, has high assimilation properties after being ingested in the large intestine due to the intestinal bacteria, and has effects of producing more short-chain fatty acids in comparison to other dietary fiber raw materials, and have further confirmed that even ingesting a yeast cell wall fraction as is has effects of inhibiting diarrhea. Thus, as a result of various researches conducted on the pharmacological effect of a yeast cell wall fraction, the present inventors have achieved this invention by discovering that a yeast cell wall fraction is capable of preventing or treating the symptoms of inflammatory bowel diseases such as ulcerative colitis, constipation, allergic diseases such as atopic dermatitis, and so on. Moreover, upon additional intense study of the yeast cell wall fraction, the present inventors have achieved this invention by discovering that the yeast cell wall fraction obtained with a simple operation of water cleansing after alkali processing yields superior effects for preventing or treating the symptoms of inflammatory bowel diseases such as ulcerative colitis, constipation, allergic diseases such as atopic dermatitis, and so on, as well as such yeast cell wall fraction being tasteless and odorless which taste and odor are characteristic to autolysis and suitable for ingestion.

SUMMARY OF THE INVENTION

The present invention is directed to a pharmacological composition having a yeast cell wall fraction as its active constituent (claim 1); a pharmacological composition according to claim 1, wherein the pharmacological composition has a yeast cell wall fraction as its active constituent and is a preventive and/or treating agent for inflammatory bowel disease (claim 2); a pharmacological composition according to claim 1, wherein the pharmacological composition has a yeast cell wall fraction as its active constituent and is a preventive and/or treating food product for inflammatory bowel disease (claim 3); a pharmacological composition according to claim 2 or claim 3, wherein the inflammatory bowel disease is ulcerative colitis (claim 4); a pharmacological composition according to claim 1, wherein the pharmacological composition has a yeast cell wall fraction as its active constituent and is a preventive and/or treating agent for constipation (claim 5); a pharmacological composition according to claim 1, wherein the pharmacological composition has a yeast cell wall fraction as its active constituent and is a preventive and/or treating food product for constipation (claim 6); a pharmacological composition according to claim 1, wherein the pharmacological composition has a yeast cell wall fraction as its active constituent and is a preventive and/or treating agent for allergic disease (claim 7); a pharmacological composition according to claim 1, wherein the pharmacological composition has a yeast cell wall fraction as its active constituent and is a preventive and/or treating food product for allergic disease (claim 8); a pharmacological composition according to claim 7 or claim 8, wherein the allergic disease is atopic dermatitis (claim 9); a pharmacological composition according to claim 7 or claim 8, wherein the allergic disease is delayed-type hypersensitivity (claim 10); a pharmacological composition according to any one of claims 1 to 10, wherein as the yeast cell wall fraction, used is a yeast cell wall fraction obtained by performing alkali treatment and water cleansing thereafter to a yeast cell or yeast extract residue, without conducting alcohol treatment and/or ozone treatment thereto (claim 11); and a pharmacological composition according to claim 11, wherein as the yeast cell or yeast extract residue, used is a yeast cell or yeast extract residue to which high-pressure homogenizer processing is performed (claim 12).

Moreover, the present invention is also directed to a yeast cell wall fraction obtained by performing alkali treatment and water cleansing thereafter to a yeast cell or yeast extract residue, without conducting alcohol treatment and/or ozone treatment thereto (claim 13); and a yeast cell wall fraction according to claim 13, wherein as the yeast cell or yeast extract residue, used is a yeast cell or yeast extract residue to which high-pressure homogenizer processing is performed (claim 14).

DESCRIPTION OF THE PREFERRED EMBODIMENTS

A yeast cell wall fraction as used herein shall mean a yeast cell wall fraction obtained by removing cell inner substance, which is soluble in water or a polar solvent, such as protein, amino acid, and nucleic acid, from yeast cells. A yeast cell wall fraction obtained by removing such soluble substance from the yeast cells may normally be prepared by conducting autolysis to the yeast cells pursuant to enzymegenation and separating and removing the soluble substance from the cells. As the method of such enzymegenation, exemplified may be so-called autolysis which uses the enzyme of yeast cells, an enzyme-adding method of adding external enzymes such as protease, nuclease, glucanase, esterase, etc., and methods combining the above may also be used. A yeast cell wall fraction may thereby be obtained by conducting removal treatment such as centrifugation to the soluble cell body substance and removing it from the enzymegenated yeast cells. As each of the aforementioned enzymegenation methods is a method used upon manufacturing the yeast cell substance as a yeast extract, from the perspective of manufacturing costs, it is advantageous to use the yeast extract residue, which is a by-product material in the yeast extract manufacture, as the yeast cell wall fraction. As such yeast cell wall fraction, used may be commercially available brewer's yeast cell walls ("Imsel BF$^R$" manufactured by Tanabe Seiyaku Co., Ltd.).

Moreover, as the yeast cell wall fraction, preferably used is the yeast cell wall fraction obtained by performing alkali treatment and water cleansing thereafter to a yeast cell or yeast extract residue, without conducting alcohol treatment and/or ozone treatment thereto. The yeast cell wall fraction obtained thereby yields superior effects for preventing or treating the symptoms of inflammatory bowel diseases such as ulcerative colitis, constipation, allergic diseases such as atopic dermatitis, and so on, as well as such yeast cell wall fraction carrying no foreign taste and odor characteristic to autolysis and suitable for ingestion. As the water cleansing treatment after the alkali treatment, it is preferable that a slurry yeast cell is alkali treated and water cleansed thereafter in the yeast extract process, the yeast extract residue obtained from the yeast cell is further alkali treated, and thereafter water cleansed. Nevertheless, it will suffice if either the yeast cell or the yeast extract residue is water cleansed and thereafter alkali treated. As the alkali treatment of the aforementioned slurry yeast cell, for example, employed may be a method wherein sodium hydroxide is added, such that the pH thereof becomes 8~12, preferably 9~10, to a yeast cell slurry prepared with a solid content concentration of 5~20% by weight, preferably 8~12% by weight, and more preferably approximately 10% by weight, and stirring this at 0~20° C., preferably 0~10° C. Moreover, as the water cleansing to be conducted after the alkali treatment, employed may be an ordinary method of water cleansing, and it is preferable that such water cleansing is conducted after dehydrating the cell with a centrifugal machine after alkali treatment from the perspective of cleansing efficiency, and such cleansing process may be performed several times. Further, as the alkali treatment of the aforementioned yeast extract residue, for example, employed may be a method wherein sodium hydroxide is added, such that the pH thereof becomes 8~12, preferably 9~10, to a yeast extract residue slurry prepared with a solid content concentration of 5~20% by weight, preferably 8~12% by weight, and more preferably approximately 10% by weight, and stirring this at 0~70° C., preferably 0~50° C., more preferably 10~30° C. Moreover, as the water cleansing to be conducted after the alkali treatment, employed may be an ordinary method of water cleansing, and it is preferable that such water cleansing is conducted after dehydrating the yeast extract residue with a centrifugal machine after alkali treatment from the perspective of cleansing efficiency, and such cleansing process may be performed several times. Causative agents of foreign taste and odor may be easily removed inexpensively with this type of water cleansing after alkali treatment without having to conduct ethanol treatment, ozone treatment, or acid treatment. As a result, obtained is a tasteless and odorless yeast cell wall fraction which may be ingested independently, as well as upon being mixed with other raw materials of food products without impairing the flavor thereof.

Further, for the purposes such as promptly conducting enzymegenation, pretreatment of physical damage of cell walls with the likes of a high-pressure homogenizer may be conducted to the yeast cell prior to enzymegenation or the aforementioned alkali treatment. It is desirable to conduct the pretreatment employing the high-pressure homogenizer, for example, under a pressure of 100–1000 kg/cm$^2$ while cooling the same.

As the yeast to be the raw material of the yeast cell wall fraction employed in the present invention, there is no particular limitation so as long as it is edible yeast and belongs to the taxonomic subdivision of yeast. Additionally employed may be brewer's yeast which is a by-product material of the brewing process, baker's yeast, alcohol yeast, sake yeast, and so on. As specific examples of such yeast, exemplified may be *Saccharomyces cerevisiae, Saccharomyces rouxii, Saccharomyces utilis,* and so on.

The pharmacological composition having a yeast cell wall fraction as its active constituent in the present invention shall mean the yeast cell wall fraction by itself or a compound of a yeast cell wall fraction and another substance or raw material, and used as a preventive and/or treating agent as well as a preventive and/or treating food product for diseases subject to the pharmacological effect of the yeast cell wall fraction.

Inflammatory bowel disease as used in the present invention shall mean the inflammatory disease of large and small intestines, which are often chronic, caused by various refractory etiology. As such inflammatory bowel diseases, exemplified may be ulcerative colitis which is an agnogenic non-specific inflammation that damages the mucous membrane of the large intestine and diffusively forms erosions and ulcers, Crohn's disease which is a non-specific granulomatous lesion involving agnogenic fibrous ulcer occurring in any and all portions of the digestive tract including the inside of the oral cavity and anus, intestinal tuberculosis characterized in granuloma involving caseation necrosis, and ischemic colitis which is an acute hemorrhagic colitis caused by the reduction or blocking of bloodstream of the intestinal tract.

Allergic disease as used in the present invention shall mean the disease developed by allergies. As such allergic diseases, exemplified may be a disease developed by an I-type (immediate) allergy, and a disease developed by a IV-type (delayed) allergy. The I-type allergy disease occurs when an IgE antibody is produced from B cells in reaction to allergen, and involves acute inflammation reaction generated by the likes of histamine isolated from the IgE sensitized mast cells and, for example, exemplified may be atopic diseases such as atopic dermatitis and atopic bronchial asthma, pollinosis, nasal allergy, anaphylactic shock, and so on. Moreover, the IV-type (delayed) allergy disease is generated by the lymphokine discharged upon the T cells sensitized with allergen contacts the same allergen for the second time and, for example, exemplified may be contact dermatitis, rejection of organ transplant, and various autoimmune diseases.

The yeast cell wall fraction of the present invention may be used as the preventive or treating material for inflammatory bowel diseases such as ulcerative colitis, constipation, allergic diseases such as atopic dermatitis, and so on by being blended with the following and used as a food product: yogurt, yogurt drinks, juices, milk, soy milk, alcohol, coffee, tea, green tea, oolong tea, refreshening beverages and other various beverages, pudding, cookies, bread, cakes, jelly, rice crackers and other baked confections, sweet jelly of beans and other Japanese sweets, frozen desserts, chewing gum and other snacks, noodles such as Japanese wheat noodles and buckwheat noodles, steamed fish paste, ham, fish meat sausage and other fish food products, bean paste, soy sauce, dressings, mayonnaise, sweeteners and other seasonings, bean curd, konnyaku jelly, fish boiled in soy sauce, steam-baked meat pie, croquette, salads and other various delicatessen. As a result, the advantages of the present invention are exhibited and, particularly, it is possible to contribute to the improvement of QOL (quality of life) of patients with an inflammatory bowel disease and so on which have dietary restrictions.

EXAMPLES

Examples of the present invention are now described in detail. Nevertheless, the technical scope of the present invention shall not be limited to the examples described below. Moreover, unless otherwise indicated, the weight of the yeast cells shown in the examples is of a weight (dry weight) in the actual state.

Preparation 1

The weight of a fermented brewer's yeast slurry obtained as a by-product material of the brewing process was precisely measured, and water was added thereafter such that the solid content became 10% by weight. This suspended solid was auto-digested at 50° C. for 17 hours under a reactive condition, centrifuged thereafter, and a yeast cell wall fraction was obtained by removing the soluble cell substance from the auto-digested residue. The protein content of this yeast cell wall fraction was 34.2% and the dietary fiber content (Southgate method) was 35.3%.

Preparation 2

The weight of a fermented brewer's yeast slurry obtained as a by-product material of the brewing process was precisely measured, and water was added thereafter such that the solid content became 10% by weight. Sodium hydroxide was added until pH9, mixed at 10° C., centrifuged thereafter, and this suspended solid, in which water was added to the sedimentary fraction, was auto-digested at 50° C. for 17 hours under a reactive condition, centrifuged thereafter, and a yeast cell wall fraction was obtained by removing the soluble cell substance from the auto-digested residue. The protein content of this yeast cell wall fraction was 31.7% and the dietary fiber content (Southgate method) was 39.2%.

Preparation 3

The weight of a fermented brewer's yeast slurry obtained as a by-product material of the brewing process was precisely measured, and water was added thereafter such that the solid content became 10% by weight. Sodium hydroxide was added until pH9, mixed at 10° C., centrifuged thereafter, water was added to the sedimentary fraction, water cleansed thereafter, and centrifuged for the second time. After water was added such that the solid content became 10% by weight, this suspended solid was auto-digested at 50° C. for 17 hours under a reactive condition, centrifuged thereafter, and a yeast cell wall fraction was obtained by removing the soluble cell substance from the auto-digested residue. The protein content of this yeast cell wall fraction was 27.8% and the dietary fiber content (Southgate method) was 44.3%.

Preparation 4

The weight of a fermented brewer's yeast slurry obtained as a by-product material of the brewing process was precisely measured, and water was added thereafter such that the solid content became 10% by weight. Sodium hydroxide was added until pH9, mixed at 10° C., centrifuged thereafter, water was added to the sedimentary fraction, water cleansed thereafter, and centrifuged for the second time. After water was added such that the solid content became 10% by weight, this suspended solid was auto-digested at 50° C. for 17 hours under a reactive condition, centrifuged thereafter, and a yeast cell wall fraction was obtained by removing the soluble cell substance from the auto-digested residue. Water was added such that the solid content of this fraction became 10% by weight and water cleansed and centrifuged thereafter, and such operation was repeated twice, and the sedimentary fraction obtained thereby was used as the yeast cell wall fraction. The protein content of this yeast cell wall fraction was 21.3% and the dietary fiber content (Southgate method) was 57.6%.

Preparation 5

The weight of a fermented brewer's yeast slurry obtained as a by-product material of the brewing process was precisely measured, and water was added thereafter such that the solid content became 10% by weight. Sodium hydroxide was added until pH9, mixed at 10° C., and centrifuged thereafter. This suspended solid in which water was added such that the solid content became 10% by weight, was auto-digested at 50° C. for 17 hours under a reactive condition, protease was further added thereto, and enzyme reaction was conducted at 50° C. for 18 hours, and centrifugation was conducted in order to remove the soluble cell substance. The sedimentary fraction obtained thereby was used as the yeast cell wall fraction. The substance analysis values of this yeast cell wall fraction are shown in Table 1.

Preparation 6

The weight of a fermented brewer's yeast slurry obtained as a by-product material of the brewing process was precisely measured, and water was added thereafter such that the solid content became 10% by weight. Sodium hydroxide was added until pH9, mixed at 10° C., and centrifuged thereafter. This suspended solid in which water was added such that the solid content became 10% by weight, was auto-digested at 50° C. for 17 hours under a reactive condition, protease was further added thereto, and enzyme reaction was conducted at 50° C. for 18 hours, and centrifugation was conducted in order to remove the soluble cell substance. Water was added such that the solid content of the sedimentary fraction obtained thereby became 10% by weight, sodium hydroxide was added until pH10, mixed at 20° C., centrifuged thereafter, water was added to the sedimentary fraction and cleansed thereafter, and centrifugation was conducted for a second time. The obtained sedimentary fraction was used as the yeast cell wall fraction.

Test Example 1

In order to compare the underwater swelling factor of the yeast cell wall fraction obtained in Preparation 5 with the swelling factor of other representative dietary fiber materials, the underwater sedimentary volume in an environment artificially reproducing the digestive organs was measured. Used as samples in addition to the yeast cell wall fraction were cellulose, wheat bran, corn fiber, beet fiber, and germinated barley fiber, 1 gram of each of these samples was placed in a 100 ml medium bottle, 50 ml of $\frac{1}{15}$M phosphate buffered liquid (4.7 g of $Na_2HPO_4$ and 4.5 g of $KH_2PO_4$ are taken, distilled water is added such that the constant volume is 1 liter, pH6.8) was added and stirred. Ultrasonic treatment and deaeration treatment were performed for 1 minute, and ultrasonic treatment was conducted continuously for 3 minutes thereafter, moved to a 100 ml graduated cylinder, and the aforementioned buffered liquid was added such that the constant volume became 100 ml. After 15 minutes of still standing, the sedimentary volume (ml/g) of the respective samples was measured. The results are shown in Table 2. As clear from Table 2, the yeast cell wall fraction showed a higher underwater swelling factor in comparison to the other representative dietary fiber materials.

Test Example 2

A test was conducted regarding the inflammatory inhibition effect on colitis of the yeast cell wall fraction using a rat colitis model. As a test specimen, SD male rats (3 weeks old, approximately 50 g body weight) were preliminarily raised for 1 week with solid foodstuff (CE-2, manufactured by Clea Japan, Inc.) and, after adaptation to the experimental environment, were used upon being separated into groups of 10 rats each. As the test foodstuff (subject samples), used were the yeast cell wall fraction group prepared in Preparation 4 of which the composition thereof is shown in Table 3 and a control group containing cellulose which is in an equal amount to the dietary fiber contained in the cell wall fraction. Moreover, ulcerative colitis was experimentally developed by partially amending the method of Iwanaga et al. (Journal of Gastroenterology 29, 430–438, 1994); specifically, 3% of dextran sulfate sodium was added to the foodstuff. The rats freely ingested the test foodstuff for a 5-day period.

Figure 1:
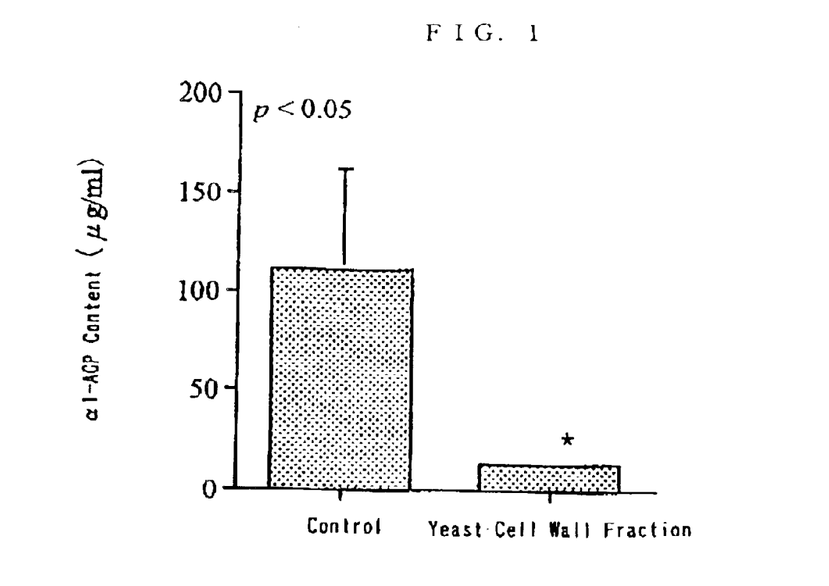
FIG. 1 is a diagram showing the measurement results of the inflammatory marker á1-AGP in the blood serum of the colitis model rat.
Figure 2:
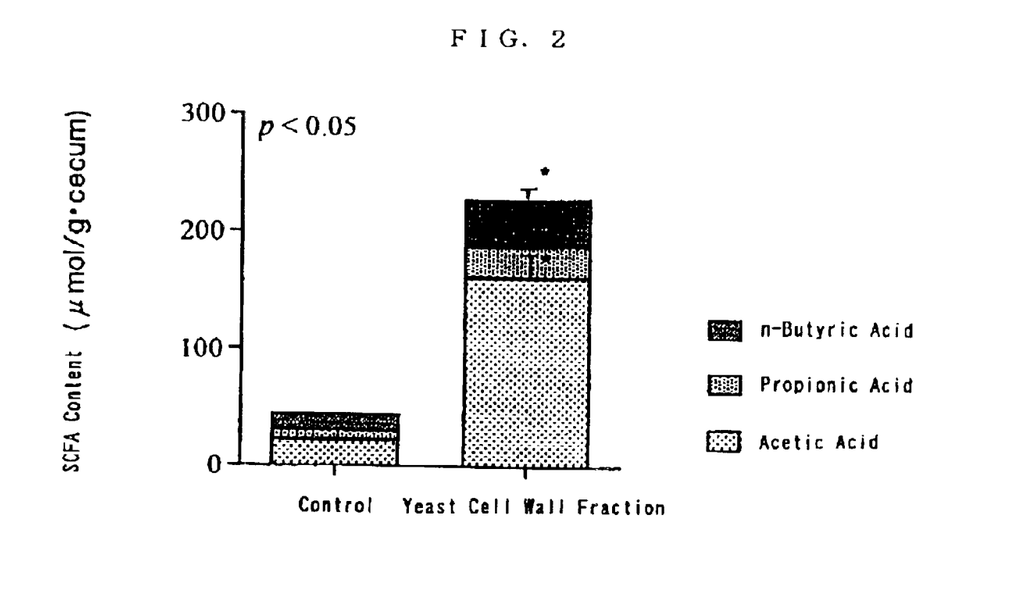
FIG. 2 is a diagram showing the measurement results of the short-chain fatty acid production in the cecum of the colitis model rat.

After administering the test foodstuff for 5 days, the conditions of fecal and anus were observed to evaluate the existence of diarrhea and melena. The results are shown in Table 4. "Number of rats with diarrhea/melena" in Table 4 shows the number of rats that developed diarrhea or melena, and "Number of rats with melena" shows the number of rats that developed only the condition of melena among the "Number of rats with diarrhea/melena". Moreover, dissection was conducted after the aforementioned observation, blood and the cecal contents were collected, and measurements of á1-AGP (Acid Glico Protein), which is an inflammation marker in the blood serum and the high value of which shows strong inflammation, and short-chain fatty acid production in the cecum were conducted. These results are shown in FIG. 1 and FIG. 2. From the aforementioned results, it was confirmed that upon ingesting a yeast cell wall fraction, the symptoms of diarrhea and melena were improved and the inflammation of the mucous membrane of the large intestine was inhibited. Further, it was confirmed that even when ingested together with an ulcerative colitis inducing agent, the yeast cell wall fraction showed effective preventing and treating effects against ulcerative colitis.

Test Example 3

Figure 3:
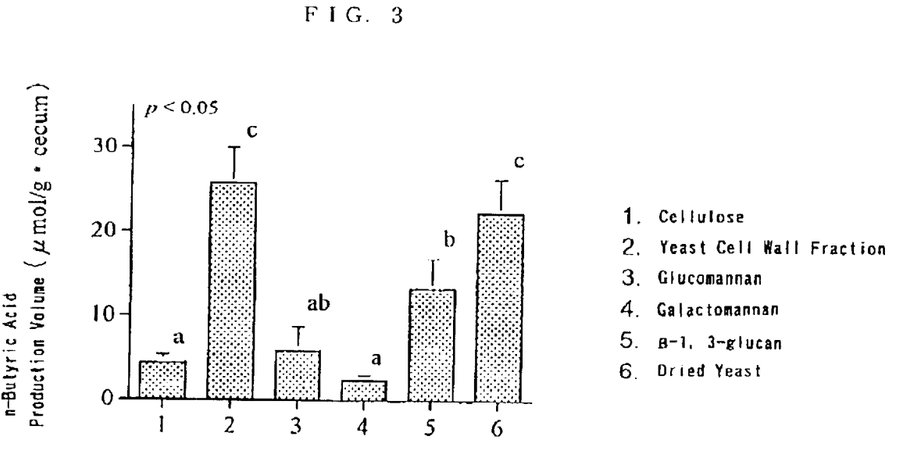
FIG. 3 is a diagram showing the measurement results of the butyric acid production in the cecum of the colitis model rat.

Next, a similar test as with Test Example 2 was conducted other than that as the test foodstuff (subject samples), used were a control group containing cellulose, a yeast cell wall fraction group prepared in Preparation 5, glucomannan group, galactomannan group, β-1, 3-glucan group, and dried yeast group. Glucomannan (manufactured by Wako Pure Chemical Industries, Ltd.), galactomannan (manufactured by Sansho Co., Ltd.), β-1, 3-glucan group (manufactured by Wako Pure Chemical Industries, Ltd.), and dried yeast group (manufactured by Kirin Brewery Co., Ltd.), were used in equal amounts as the dietary fiber content of the yeast cell wall fraction. After administering the test foodstuff for 5 days, the conditions of fecal and anus were observed to evaluate the existence of diarrhea and melena. The results are shown in Table 5. "Number of rats with diarrhea/melena" in Table 5 shows the number of rats that developed diarrhea or melena, and "Number of rats with melena" shows the number of rats that developed only the condition of melena among the "Number of rats with diarrhea/melena". Moreover, dissection was conducted after the aforementioned observation, blood and the cecum contents were collected, and the butyric acid production in the cecum was measured. These results are shown in FIG. 3. According to FIG. 3, the dried yeast group shows an approximate butyric acid production in the cecum as with the yeast cell wall fraction group. Nevertheless, as clear from Table 5, the yeast cell wall fraction group yields superior improvement results on diarrhea and melena in comparison to the dried yeast group with respect to the "Number of rats with diarrhea/melena" and "Number of rats with melena".

Test Example 4

Next, test was conducted on the anti-atopic dermatitis effect of the yeast cell wall fraction. As a test specimen, NC/Nga mice (5.5 weeks old) were preliminarily raised for 2 weeks with solid foodstuff (CE-2, manufactured by Clea Japan, Inc.) and, after adaptation to the experimental environment, were used upon being separated into groups of 7 mice each. When raised under ordinary conditions, NC/Nga mice develop symptoms similar to atopic dermatitis pursuant to their growth, the plasma IgE concentration in the blood rises, and are used as models for atopic dermatitis (Molecular Medicine, Vol. 34, No. 12, 1997, 1554–1557). Moreover, as the test foodstuff, used are the compositions shown in Table 6; namely, the yeast cell wall fraction group obtained in Preparation 4; a raffinose group, which is oligosaccharide, reported as having treating effects for atopic dermatitis ("Food Industry" 1999–2.28, p29–35); and control groups that do not contain the above; and the administration of the test foodstuff to the test mice were continued until the end of the test. Hapten sensitization was conducted 1 week after the commencement of test foodstuff administration, and the initial (first) hapten challenge was conducted a week thereafter, and a hapten challenge was conducted for each elapsed week thereafter, and the final (eighth) hapten challenge was conducted 8 weeks after the commencement of test foodstuff administration. Hapten sensitization was conducted by applying picryl chloride 7% by weight ethanol solution 100 μl to the abdomen, and the hapten challenge was conducted by applying picryl chloride 1% by weight olive oil solution 10 μl to both faces of each auricle portion.

Figure 4:
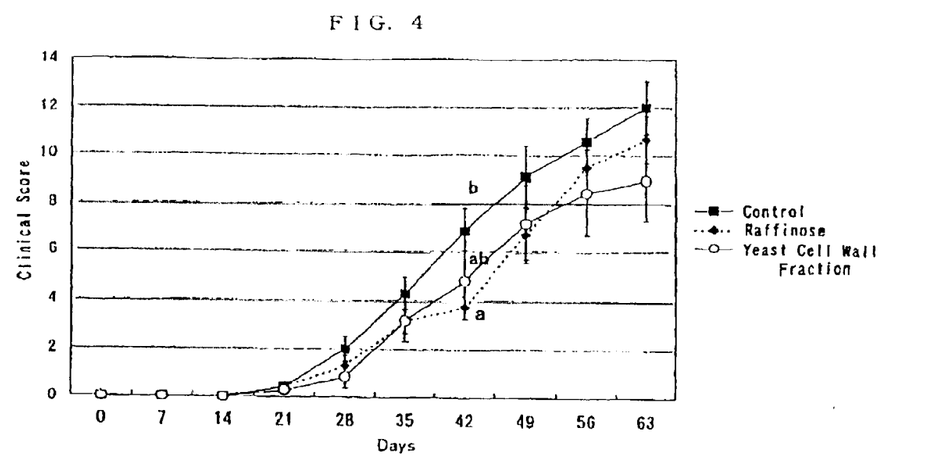
FIG. 4 is a diagram showing the variation with time of the clinical score after the hapten challenge in the anti-atopic dermatitis test.
Figure 5:
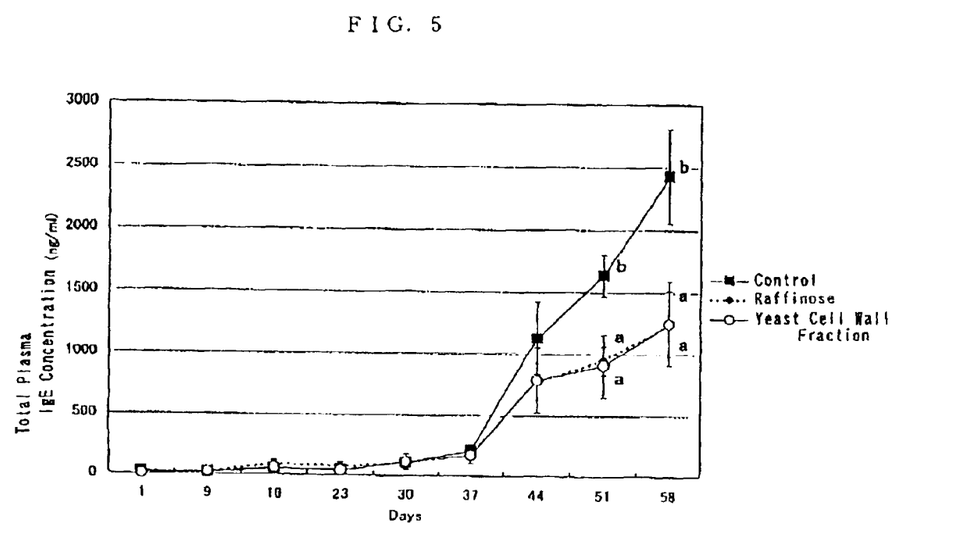
FIG. 5 is a diagram showing the variation with time of the total plasma IgE level after the hapten challenge in the anti-atopic dermatitis test.

In the aforementioned anti-atopic dermatitis test, the clinical score and total plasma IgE level were measured with time. The observation of the clinical score was conducted 10 times; specifically, at the time of hapten sensitization, each hapten challenge (total of 8 times), and 1 week after the final hapten challenge. The clinical score was comprehensively evaluated in three evaluation phases of score (0)none, (1)mild, (2)moderate, (3)severe, regarding the 5 symptoms of acomia of scalp; bleeding and erosion of scalp; bleeding and erosion of auricle portion; corpulence, edema, and purpura of auricle portion; and deformation and disappearance of auricle porition. The results are shown in FIG. 4. Moreover, the measurement of the total plasma IgE concentration in the blood which shows the correlation of the generation of inflammation and its production was conducted by collecting blood 9 times from retro-orbital plexues; namely on the following day of the hapten sensitization and two days after the respective hapten challenges (total of 8 times), and using an IgE measurement kit ("Yamasa EIA" manufactured by Yamasa Corporation). The results are shown in FIG. 5 ($p<0.05$). In addition, the weight and daily foodstuff ingestion amount of the donor mice prior to the commencement and after the completion of the administration of the test foodstuff are shown in Table 7 ($p<0.05$).

From FIG. 4 and FIG. 5, it is clear that the yeast cell wall fraction group shows similar behavior as with the raffinose group when measured with time in the clinical score and total plasma IgE concentration in the blood and, in comparison to the control group, possesses significantly superior anti-atopic dermatitis effects.

Test Example 5

The same test mice and test foodstuff as in Test Example 4 were used to conduct a test on the inhibition effect of delayed-type hypersensitivity. The NC/Nga mice, as described above, are known as a model for atopic dermatitis, but can also be used as a model for delayed-type hypersensitivity. The administration of test foodstuff to the test mice was continued until the end of the test. Hapten sensitization was conducted 1 week after the commencement of the foodstuff administration, hapten challenge was conducted 1 week thereafter upon measuring the thickening of the auricle portion prior to the challenge, and measurement of the thickening of the auricle portion 24 hours later was conducted once again. Hapten sensitization was conducted by applying picryl chloride 7% by weight ethanol solution 100 μl to the abdomen, and the hapten challenge was conducted by applying picryl chloride 1% by weight olive oil solution 10 μl to both faces of each auricle portion.

Figure 6:
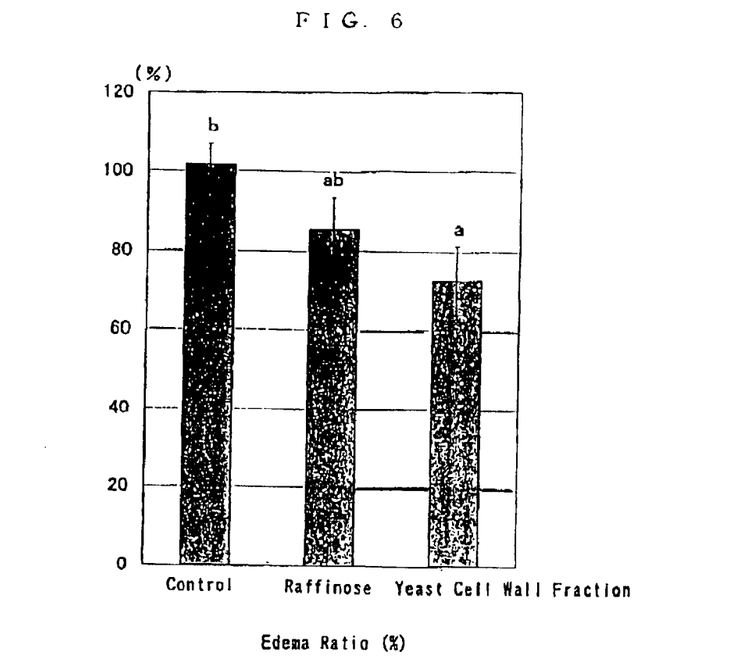
FIG. 6 is a diagram showing the measurement results of the edema ratio representing the percentage of change in the thickness of the auricle portion pursuant to the hapten challenge in the skin irritation test.
Figure 7:
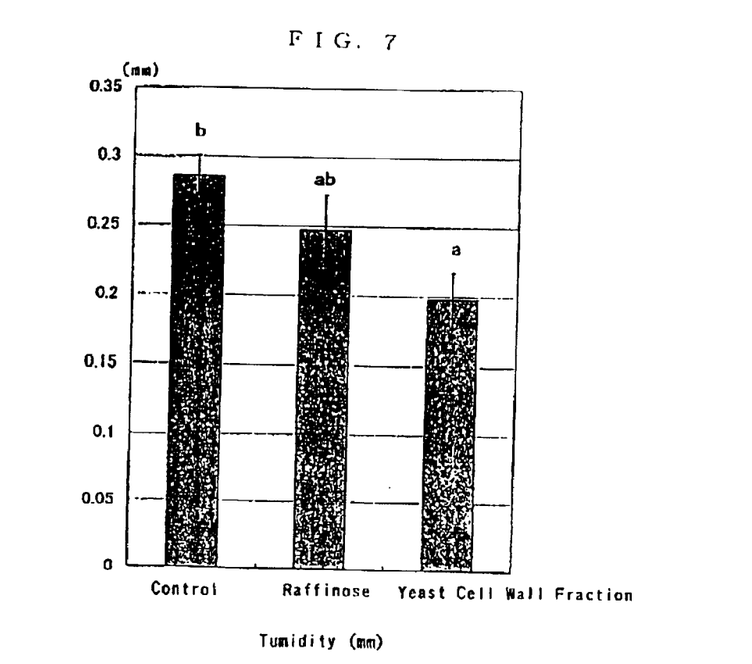
FIG. 7 is a diagram showing the measurement results of the tumidity representing the percentage of change in the thickness of the auricle portion pursuant to the hapten challenge in the skin irritation test.
Figure 8:
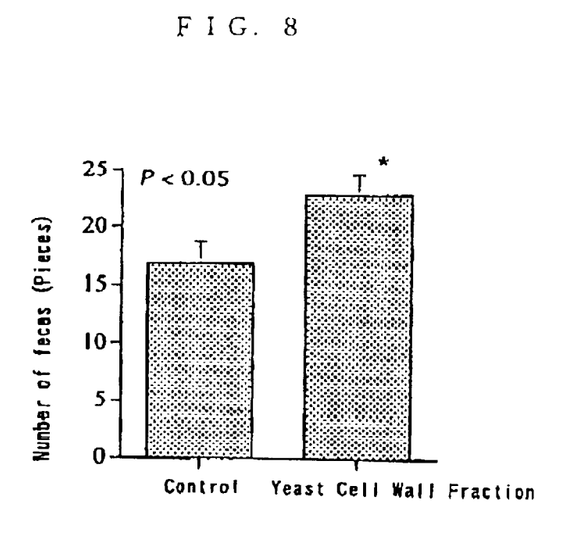
FIG. 8 is a diagram showing the measurement results of the number of feces of the constipated model rat during the 3-day period.
Figure 9:
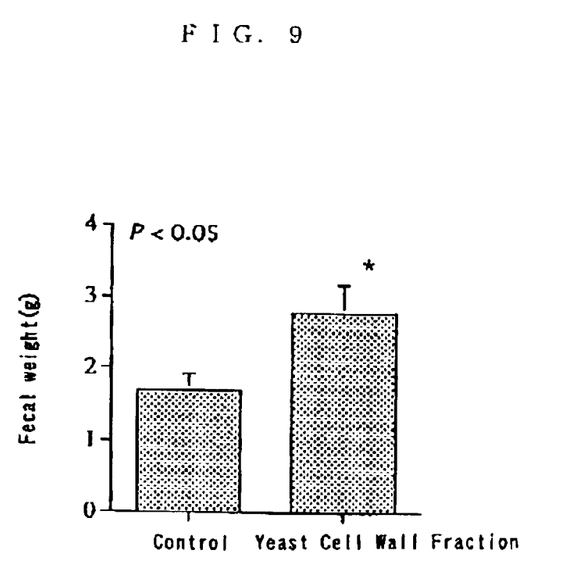
FIG. 9 is a diagram showing the measurement results of the fecal weight of the constipated model rat during the 3-day period.
Figure 10:
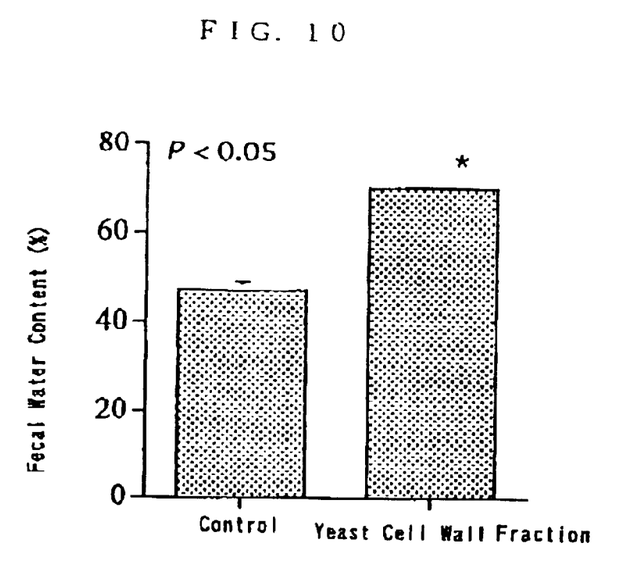
FIG. 10 is a diagram showing the measurement results of the fecal water content regarding the fresh feces after dissection of the constipated model rat.
Figure 11:
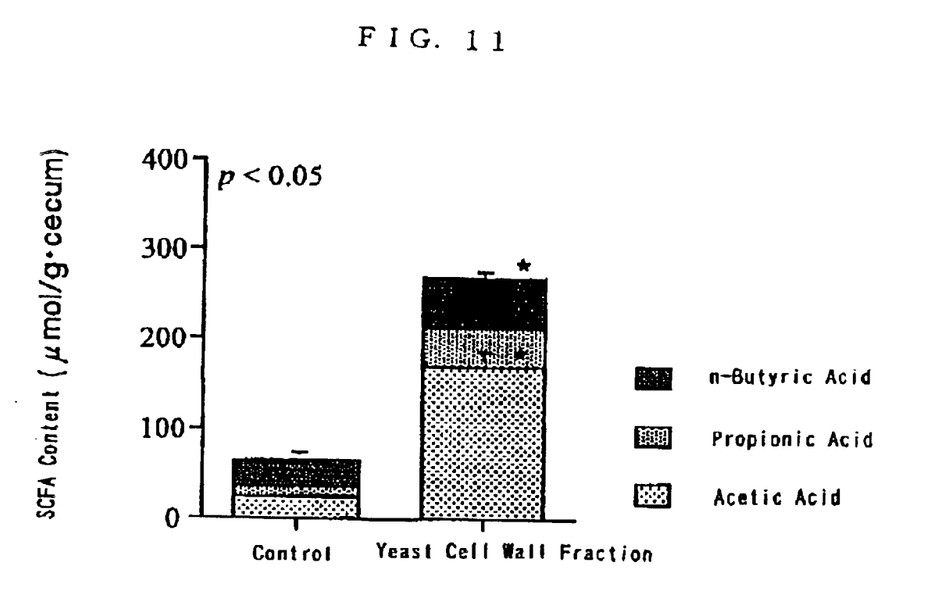
FIG. 11 is a diagram showing the measurement results of the short-chain fatty acid production in the cecum of the constipated model rat.

The anti-inflammation effect was measured by seeking the edema ratio and tumidity from the aforementioned test results. The edema ratio represents the percentage of the change in thickness of the auricle portion to which hapten has been applied, and is a value that can be sought by edema ratio=(thickness of auricle portion after challenge−thickness of auricle portion prior to challenge)/thickness of auricle portion prior to challenge×100. In addition, tumidity represents the change in thickness of the auricle portion to which hapten has not been applied, and is a value that can be sought by tumidity(mm)=(thickness of hapten-applied auricle portion after challenge−thickness of auricle portion scheduled for hapten application prior to challenge)−(thickness of control auricle portion after challenge−thickness of control auricle portion prior to challenge), and both values are indices ordinarily used to judge the inhibition effect of inflammation. The result are shown in FIG. 6 and FIG. 7 ($p<0.05$). In addition, the weight and daily foodstuff ingestion amount of the donor mice prior to the commencement and after the completion of the administration of the test foodstuff are shown in Table 8 ($p<0.05$).

From these results, it is clear that the yeast cell wall fraction group has a significantly superior anti-inflammation effect in comparison to the raffinose group and control group. Thus, it has been cleared that the yeast cell wall fraction is effective in delayed-type hypersensitivity such as contact dermatitis, tuberculosis, rejection of organ transplant, and various autoimmune diseases.

Test Example 6

A test was conducted regarding the preventive effect of constipation upon utilizing the yeast cell wall fraction obtained in Preparation 4. As a test specimen, SD male rats (3 weeks old, around 50 g body weight) were preliminarily raised for 1 week with solid foodstuff (CE-2, manufactured by Clea Japan Inc.) and, after adaptation to the experimental environment, were used upon being separated into groups of 10 rats each. As the test foodstuff (subject samples), used were the yeast cell wall fraction group and control group of which the compositions thereof are shown in Table 9. The rats freely ingested the test foodstuff. Moreover, loperamide hydrochloride was mixed with the foodstuff to experimentally develop constipation. After administrating the test foodstuff for 11 days, foodstuff to which loperamide hydrochloride 0.01% by weight was mixed to the test foodstuff shown in Table 9 was administered for 3 days.

Fecal was collected for the 3 days during which the loperamide hydrochloride-mixed foodstuff was administered. Further, fresh fecal and cecal contents were collected pursuant to dissection, and the number of feces, fecal weight, fecal water content, and the short-chain fatty acid (SCFA) production in the cecum were measured. These results are shown in FIGS. 8–11. As clear from FIGS. 8–11, when a yeast cell wall fraction is ingested, values in the number of feces (FIG. 8), fecal weight (FIG. 9), and fecal water content (FIG. 10) are all larger in comparison to the control group, and shows that there is a constipation preventive and improvement effect. Moreover, even in the measurement value (FIG. 11) of the short-chain fatty acid production in the cecum, the yeast cell wall fraction group showed a higher value than the control group.

According to the present invention, it is possible to provide a pharmacological composition as a raw material capable of preventing or treating the symptoms of inflammatory bowel diseases such as ulcerative colitis, constipation, allergic diseases such as atopic dermatitis, and so on, and which has little side effect and thereby safe, high water dispersibility, and can be ingested easily.

TABLE 1

| Protein | Crude Fat | Crude Fiber | Ash Content | Nitrogen-Free Extracts |
|---|---|---|---|---|
| 27.7 | 3.8 | 21.1 | 3.9 | 43.5 |

| Dietary Fiber (AOAC Method) | Dietary Fiber (Southgate Method) |
|---|---|
| 56.0 | 59.4 |

Unit: percentage by weight

TABLE 2

| Subject Sample | Underwater Sedimentary Volume (ml/g) |
|---|---|
| Cellulose | 6 |
| Wheat Bran | 4 |
| Corn Fiber | 6 |
| Beet Fiber | 13 |
| Germinated Barley Fiber | 17 |
| Yeast Cell Wall Fraction | 50 |

TABLE 3

<Foodstuff Composition>

| | Control Group | Yeast Cell Wall Fraction Group |
|---|---|---|
| Casein | 14.6 | 11.8 |
| AIN93 Mineral Mixture | 3.5 | 3.5 |
| AIN93 Vitamin Mixture | 1 | 1 |
| Starch | 67 | 65.5 |
| Corn Oil | 5 | 5 |
| Cellulose | 5.7 | — |
| 2nd Preparative Example of Yeast Cell Wall Fraction | — | 10 |
| Dextran Sulfate Sodium | 3 | 3 |
| Choline Chloride | 0.2 | 0.2 |
| TOTAL | 100 | 100 |

TABLE 4

| Subject Sample | Number of rats with diarrhea/melena | Number of rats with melena | Number of rats with loose stool |
|---|---|---|---|
| Control | 8/10 | 5/10 | 2/10 |
| Yeast Cell Wall Fraction | 0/10 | 0/10 | 3/10 |

TABLE 5

| Subject Sample | Number of rats with diarrhea/melena | Number of rats with melena | Number of rats with loose stool |
|---|---|---|---|
| Control | 9/10 | 7/10 | 1/10 |
| Yeast Cell Wall Fraction | 3/10 | 0/10 | 2/10 |
| Glucomannan | 10/10 | 8/10 | 0/10 |
| Galactomannnan | 10/10 | 5/10 | 0/10 |
| β-1,3-glucan | 9/10 | 6/10 | 1/10 |
| Dried Yeast | 9/10 | 4/10 | 1/10 |

TABLE 6

<Foodstuff Composition>

| | Control Group | Raffinose Group | Yeast Cell Wall Fraction Group |
|---|---|---|---|
| Casein | 20 | 20 | 17 |
| DL-methionine | 0.3 | 0.3 | 0.3 |
| Corn Starch | 54 | 54 | 53 |
| Sucrose | 10 | 10 | 10 |
| Cellulose Powder | 6 | — | — |
| Corn oil | 5 | 5 | 5 |
| AIN93 Mineral Mixture | 3.5 | 3.5 | 3.5 |
| AIN93 Vitaine mixture | 1 | 1 | 1 |
| Bitartrate Choline | 0.2 | 0.2 | 0.2 |
| Raffinose | — | 6 | — |
| Yeast Cell Wall Fraction | — | — | 10 |
| TOTAL | 100 | 100 | 100 |

TABLE 7

Test Results of Anti-Atopic Dermatitis

| | Control Group | | Raffinose Group | | Yeast Cell Wall Fraction Group | |
|---|---|---|---|---|---|---|
| | Mean | SE | Mean | SE | Mean | SE |
| Ingestion (g/day) | 4.26b | 0.06 | 4.05ab | 0.13 | 3.98a | 0.07 |
| Initial Weight (g) | 23.8 | 0.7 | 23.9 | 0.6 | 23.6 | 0.8 |
| Final Weight (g) | 27.2 | 1.0 | 25.9 | 1.3 | 28.2 | 0.8 |

TABLE 8

Test Results of Anti-Delayed-type hypersensitivity

| | Control Group | | Raffinose Group | | Yeast Cell Wall Fraction Group | |
|---|---|---|---|---|---|---|
| | Mean | SE | Mean | SE | Mean | SE |
| Ingestion (g/day) | 4.1 | 0.1 | 4.2 | 0.1 | 3.8 | 0.1 |
| Initial Weight (g) | 23.8 | 0.7 | 23.9 | 0.6 | 23.6 | 0.8 |
| Final Weight (g) | 24.3 | 0.6 | 24.2 | 0.6 | 23.5 | 1.3 |

TABLE 9

<Foodstuff Composition>

| | Control Group | Yeast Cell Wall Fraction Group |
|---|---|---|
| Casein | 14.6 | 13.5 |
| AIN93 Vitamin Mixture | 1.0 | 1.0 |
| AIN93 Mineral Mixture | 3.5 | 3.5 |
| Choline Chloride | 0.2 | 0.2 |
| Cellulose | 2.9 | — |
| Yeast Cell Wall Fraction | — | 5.0 |
| Loperamide Hydrochloride | 0.01 | 0.01 |
| Corn Oil | 5.0 | 5.0 |
| Corn Starch | 72.79 | 71.79 |
| TOTAL | 100 | 100 |

What is claimed is:

1. A method for treating a disease, disorder or condition selected from the group consisting of inflammatory bowel disease, constipation and allergic disease, comprising orally administrating an effective amount of yeast cell wall fraction to a mammal, wherein the yeast cell wall faction is obtained by a process comprising:

a) treating a yeast cell or a yeast extract residue with alkali, and b) cleansing the yeast cell or yeast extract residue with water, thereby removing any water-soluble substance from yeast cells.

2. The method according to claim 1, wherein the disease, disorder or condition is an inflammatory bowel disease.

3. The method according to claim 2, wherein the inflammatory bowel disease is ulcerative colitis.

4. The method according to claim 1, wherein the disease, disorder or condition is constipation.

5. The method according to claim 1 wherein the disease, disorder or condition is an allergic disease.

6. The method according to claim 5, wherein the allergic disease is atopic dermatitis.

7. The method according to claim 5, wherein the allergic disease is delayed-type hypersensitivity.

8. The method according to claim 1, wherein the process further comprises high-pressure homogenizer processing.

* * * * *